US005736563A

United States Patent [19]
Richter

[11] Patent Number: 5,736,563
[45] Date of Patent: *Apr. 7, 1998

[54] TRANSCUTANEOUS IN VIVO ACTIVATION OF PHOTOSENSITIVE AGENTS IN BLOOD

[75] Inventor: Anna M. Richter, Vancouver, Canada

[73] Assignee: Quadra Logic Technologies, Inc., Vancouver, Canada

[*] Notice: The term of this patent shall not extend beyond the expiration date of Pat. No. 5,484,803.

[21] Appl. No.: 555,235

[22] Filed: Nov. 8, 1995

Related U.S. Application Data

[63] Continuation of Ser. No. 384,440, Feb. 2, 1995, Pat. No. 5,484,803, which is a continuation of Ser. No. 948,113, Sep. 21, 1992, abandoned.

[51] Int. Cl.$^6$ .................................................. A61K 31/41
[52] U.S. Cl. ........................ 514/410; 514/185; 514/253; 514/455; 514/561; 540/145; 544/300; 544/306; 549/282
[58] Field of Search ...................................... 544/300, 306; 549/282; 540/145; 514/185, 253, 455, 561, 410

[56] References Cited

U.S. PATENT DOCUMENTS

| | | | |
|---|---|---|---|
| 4,866,168 | 9/1989 | Dougherty et al. | 540/145 |
| 4,960,408 | 10/1990 | Klainer et al. | 604/4 |
| 5,095,030 | 3/1992 | Levy et al. | 514/410 |

FOREIGN PATENT DOCUMENTS

| | | | |
|---|---|---|---|
| WO90/06314 | 6/1990 | WIPO | 514/410 |

OTHER PUBLICATIONS

Ben–Hur et al., Int. J. Radiat. Biol. 54(1), pp. 21–30, 1988.

Cohen et al., Cancer Res. 26, pp. 1769–1773, 1966.

Doss, Editor, Diagnosis and Theraphy of Porphyrins and Lead Intoxication, Springer–Verlag, Berlin, pp. 229–235, 1978.

Ho et al., Photochemistry and Photobiology, 54(1), pp. 83–87, 1991.

Kostron et al., Journal of Neuro–Oncology, 6, pp. 185–191, 1988.

Richter et al., Photochemistry and Photobiology, 52(3), pp. 495–500, 1990.

Kessel et al., Photochemistry and Photobiology, 53(4), pp. 475–479, 1991.

North et al, Blood Cells 18:129–40, 1992.

Jamieson et al., Leukemia Res 14:208–19, 1990.

*Primary Examiner*—Richard L. Raymond
*Attorney, Agent, or Firm*—Morrison & Foerster LLP

[57] ABSTRACT

A method destroys or impairs target cells that have selectively accumulated a photosensitizing agent. The target cells are in the bloodstream of an intact animal, which bloodstream and animal further contain non-target cells. Radiation is applied transcutaneously to at least a portion of the intact animal at an intensity effective to impair or destroy selectively the target cells and to leave non-target cells relatively unimpaired. Target cells include leukemia cells, virus-containing cells, parasite-containing cells, and microorganisms such as bacteria, parasites and free viruses.

8 Claims, 6 Drawing Sheets

TRANSCUTANEOUS IN VIVO ACTIVATION OF PHOTOSENSITIVE AGENTS IN BLOOD

This application is a continuation, application Ser. No. 08/384,440 filed 2 Feb. 1995, now U.S. Pat. No. 5,484,803 which in turn is a continuation of application Ser. No. 07/948,113 filed Sep. 21, 1992, now abandoned.

FIELD OF THE INVENTION

This invention relates generally to the field of medicine and pharmacotherapeutics with photosensitizing agents. Specifically, the invention is a method of destroying or impairing blood-borne target cells which have taken up a photosensitizing agent by applying radiation transcutaneously to selectively impair or destroy the target cells and leave non-target cells relatively unimpaired.

BACKGROUND OF THE INVENTION

Photodynamic therapy involves the administration of a photosensitizing compound and subsequent irradiation with light of tissue to which the photosensitizing compound has selectively homed. The target tissue containing a sufficiently high concentration of the photosensitizing compound selectively absorbs the light which results in impairment or destruction of the immediately surrounding cells. U.S. Pat. No. 5,095,030 describes procedures wherein photosensitizing compounds are administered to animals which are subsequently irradiated using external light sources. For example, Example 5 of this patent describes subcutaneous injection of mice with P815 tumor cells which grow into a palpable tumor. Photosensitizing compounds are then injected, and after the animals are maintained in the dark for three hours, their tumors were exposed to a strong light. The survival rates of the treated animals were improved over untreated controls. Similarly, Example 8 of that patent describes use of a rhabdomyosarcoma system in mice with a similar protocol. Thus, these examples are directed to the treatment of localized solid tumors where the externally applied light is trained on the tumor. In these instances, the target tissue is not contained in the bloodstream where the treatment must avoid damage to the blood vessels and non-targeted blood cells.

U.S. Pat. No. 4,960,408 discloses the treatment of contents of the bloodstream (HIV virus and infected T-cells) by photopheresis. In this technique the patient's blood is routed through an extracorporeal apparatus in which the white cell fraction of the blood is exposed to ultraviolet light before the white cells are returned to the patient.

Benzoporphyrin derivatives (BPD), in combination with red light (400–900 nm), have been reported to be effective in eliminating both free viruses and virally infected cells from spiked blood products and from whole blood obtained from viremic cats. Red blood cells appeared viable after the virucidal treatment. North et al. *Blood Cells* 18:129–40, 1992.

BPD also has a demonstrated higher affinity for tumor tissue, including leukemic cells, than for normal non-malignant cells. Jamieson et al., *Leukemia Res.* 14:209–19, 1990.

U.S. Pat. No. 5,095,030, issued 10 Mar. 1992, which is incorporated herein in its entirety by reference, discloses and claims various wavelength-specific cytotoxic agents which are generically described as "green porphyrins." These compounds are porphyrin derivatives which are modified by a Diels Alder reaction effectively to shift the wave length of absorption to a longer wavelength. This results in some favorable properties as compared to, for example, hematoporphyrin derivative when these compounds are employed in photodynamic therapy generally. As described in this patent, these cytotoxic agents, when administered systemically, "home" to unwanted cells, in particular to tumor cells or pathogenic viruses and subsequent irradiation with light absorbed in by these compounds causes them to transition in such a way as to effect cytotoxicity.

Pending application Ser. No. 07/832,542, filed Feb. 5, 1992, discloses the preparation of liposomes of porphyrin photosensitizers.

SUMMARY OF THE INVENTION

This invention provides a method to destroy or impair target cells that have selectively accumulated a photosensitizing agent, wherein the target cells are in the bloodstream of an intact animal. The bloodstream and animal also contain non-target cells. The method comprises applying radiation transcutaneously to at least a portion of the intact animal at an intensity effective to impair or destroy selectively the target cells, leaving non-target cells relatively unimpaired.

In another embodiment, the invention is applied to target cells which are more rapidly multiplying than are the non-target cells. In another embodiment, the target cells may be leukemia cells, virus-containing cells, parasite-containing cells, bacteria, free viruses,or other infectious agents within the blood.

While this invention provides for the use of any photosensitizing agent, preferably the agent is selected from chlorins (such as chlorin e6), bacteriochlorins, phthalocyanines, porphyrins, purpurins, merocyanines, psoralens, and pro-drugs such as δ-aminolevulinic acid which can produce drugs such as protoporphyrin in tissue. In other embodiments, BPD-MA and porfimer sodium are the photosensitizing agents.

BRIEF DESCRIPTION OF THE INVENTION

Figure 1A:
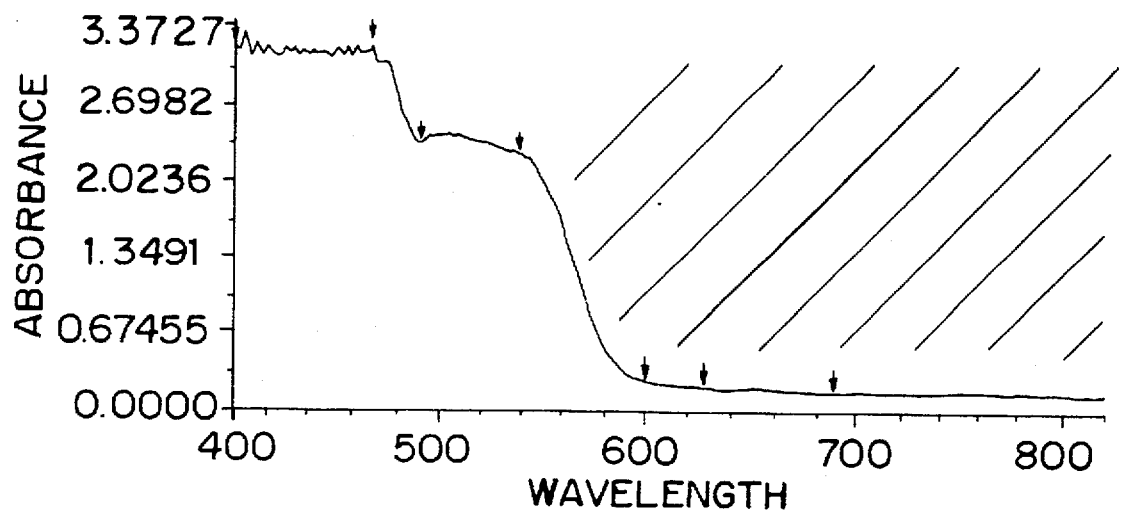
FIG. 1A shows the spectrum of light delivered by the light box.

This invention is a method of destroying or impairing blood-borne target cells that have selectively accumulated a photosensitizing agent while leaving non-target cells relatively unimpaired. The method comprises applying radiation transcutaneously to at least a portion of an intact animal at an intensity effective to impair or destroy selectively the target cells.

As used herein "target cells" are those that are intended to be impaired or destroyed by this treatment method. Target cells take up the photosensitizing agent; then when sufficient radiation is applied, the target cells are impaired or destroyed. Target cells may be any of the cells found in the blood. Target cells include, but are not limited to, leukemia cells, virus-containing cells, and parasite-containing cells. Also included among target cells are cells undergoing rapid division as compared to non-target cells. The term "target cells" also includes, but is not limited to, microorganisms such as bacteria, viruses, parasites and other infectious agents. Thus, the term "target cell" is not limited to living cells but also includes infectious particles such as viruses.

"Non-target cells" are all the cells of an intact animal which are not intended to be impaired or destroyed by the treatment method. These non-target cells include but are not limited to healthy blood cells, the normal cells making up the blood vessel(s) subjected to radiation, the cells in tissue underlying or overlying the blood vessels subjected to radiation.

"Destroy" is used to mean kill the desired target cell. "Impair" means to change the target cell in such a way as to interfere with its function. For example, North et al. observed that after exposure of BPD-treated, virus-infected T cells to light, holes developed in the T cell membrane, which increased in size until the membrane completely decomposed (*Blood Cells* 18:129–40, 1992). Target cells are understood to be impaired or destroyed even if the target cells are ultimately disposed of by macrophages.

"Photosensitizing agent" is a chemical compound which homes to one or more types of selected target cells and, when contacted by radiation, absorbs the light, which results in impairment or destruction of the target cells. Virtually any chemical compound that homes to a selected target and absorbs light may be used in this invention. Preferably, the chemical compound is nontoxic to the animal to which it is administered or is capable of being formulated in a nontoxic composition. Preferably, the chemical compound in its photodegraded form is also nontoxic. A comprehensive listing of photosensitive chemicals may be found in Kreimer-Birnbaum, *Sem. Hematol.* 26:157–73, 1989. Photosensitive compounds include, but are not limited to, chlorins, bacteriochlorins, phthalocyanines, porphyrins, purpurins, merocyanines, psoralens and pro-drugs such as δ-aminolevulinic acid, which can produce drugs such as protoporphyrin. Preferred are benzoporphyrin derivatives (BPD) and porfimer sodium. Most preferred is the benzoprophyrin derivative monoacid ring A (BPD-MA).

"Radiation" as used herein includes all wave lengths. Preferably, the radiation wave length is selected to match the wave length(s) which excites the photosensitive compound. Even more preferably, the radiation wave length matches the excitation wave length of the photosensitive compound and has low absorption by the non-target cells and the rest of the intact animal, including blood proteins. For example, the preferred wave length for BPD-MA is the range of 600–900 nm.

The radiation is further defined in this invention by its intensity, duration, and timing with respect to dosing with the photosensitive agent. The intensity must be sufficient for the radiation to penetrate skin and reach the blood-borne target cells. The duration must be sufficient to photoactivate enough photosensitive agent to act on the target cells. Both intensity and duration must be limited to avoid overtreating the animal. Timing with respect to dosing with the photosensitive agent is important, because 1) the administered photosensitive agent requires some time to home in on target cells and 2) the blood level of many photosensitive agents decreases rapidly with time.

This invention provides a method of treating an animal, which includes, but is not limited to, humans and other mammals. The term "mammals" also includes farm animals, such as cows, hogs and sheep, as well as pet or sport animals such as horses, dogs and cats.

By "intact animal" is meant that the whole, undivided animal is available to be exposed to radiation. No part of the animal is removed for separate radiation, in contrast with photophoresis, in which the animal's blood is circulated outside its body for exposure to radiation. The entire animal need not be exposed to radiation. Only a portion of the intact animal may or need be exposed to radiation. Practically speaking, radiation of areas with blood vessels close to the surface may be preferable for selective radiation.

"Transcutaneously" is used herein as meaning through the skin of an animal.

Briefly, the photosensitizing agent is generally administered to the animal before the animal is subjected to radiation.

Preferred photosensitizing agents include, but are not limited to, chlorins, bacteriochlorins, phthalocyanines, porphyrins, purpurins, merocyanines, psoralens and pro-drugs such as δ-aminolevulinic acid, which can produce drugs such as protoporphyrin. More preferred are benzoporphyrin derivatives (BPD) and porfimer sodium. Most preferred is the benzoprophyrin derivative monoacid ring A (BPD-MA).

The photosensitizing agent is administered locally or systemically. The photosensitizing agent is administered orally or by injection which may be intravenous, subcutaneous, intramuscular or intraperitoneal. The photosensitizing agent also can be administered enterally or topically via patches or implants.

The photosensitizing agent can be synthesized as a dimer, to absorb more light on a per mole basis. The photosensitizing agent also can be conjugated to specific ligands reactive with a target, such as receptor-specific ligands or immunoglobulins or immunospecific portions of immunoglobulins, permitting them to be more concentrated in a desired target cell or microorganism. This conjugation may permit lowering of the required dose level since the material is more selectively target and less is wasted in distribution into other tissues whose destruction must be avoided.

The photosensitizing agent can be administered in a dry formulation, such as pills, capsules, suppositories or patches. The photosensitizing agent also may be administered in a liquid formulation, either alone with water, or with pharmaceutically acceptable excipients, such as are disclosed in *Remington's Pharmaceutical Sciences*. The liquid formulation also can be a suspension or an emulsion. In particular, liposomal or lipophilic formulations are most desirable. If suspensions or emulsions are utilized, suitable excipients include water, saline, dextrose, glycerol, and the like. These compositions may contain minor amounts of nontoxic auxiliary substances such as wetting or emulsifying agents, antioxidants, pH buffering agents, and the like.

The dose of photosensitizing agent will vary with the target cell(s) sought, the optimal blood level (see Example 2), the animal's weight and the timing of the radiation. Depending on the photosensitizing agent used, an equivalent optimal therapeutic level will have to be established. Preferably, the dose is calculated to obtain a blood level between about 0.01 and 100 µg/ml. Preferably, the dose will obtain a blood level between about 0.01 and 10 µg/ml. When the photosensitizing agent is BPD-MA, the blood level is preferably between about 0.01 and 4 µg/ml. More preferably, a BPD-MA blood level of about 0.01 to 2 µg/ml is attained.

The intensity of radiation within the bloodstream is preferably between about 2 and 150 mW/cm$^2$. More preferably, the intensity of radiation within the bloodstream is between about 10 and 100 mW/cm$^2$. Most preferably, the intensity of radiation within the bloodstream is between about 15 and 70 mW/cm$^2$.

The duration of radiation exposure is preferably between about 0.25 minute and 24 hours. More preferably, the duration of radiation exposure is between about 0.25 minute and 6 hours. Most preferably, the duration of radiation exposure is between about 0.25 minute and 2 hours.

While not wishing to be limited by a theory, the inventor proposes that BPD can be substantially photoactivated in blood within a relatively short period of time and without excess toxicity. Thus, there appears to be a therapeutic window bounded by BPD dosage and radiation dosage. The formation of photodegradation products of BPD was used as an indicator of photoactivation. Photoactivation of BPD has been postulated to cause the formation of singlet oxygen, which has a cytotoxic effect. In view of problems related to either extracorporeal treatment of blood or intravenous light activation by means of fiberoptics, the envisaged whole body irradiation in a "red light bed" of BPD-injected patients appears to be an attractive approach to the treatment of infectious agents in blood.

The examples which follow are intended to demonstrate the efficacy of the invention and to assist in the practice of the invention. The following examples cover one photosensitizing agent and provide a means to screen other photosensitizing agents or new compounds for use in the inventive method. The following examples are intended only to be examples and not to limit the invention in any way.

General Comments

The following general comments on Materials and Procedures apply to Examples 1–4, unless otherwise noted.

Materials

BPD-MA was synthesized as described in U.S. Pat. Nos. 4,920,143 and 4,883,790, incorporated herein by reference. BPD-MA was obtained from QuadraLogic Technologies, Inc. and stored dissolved in DMSO (4.5 mg/ml) at −70° C. Liposomal BPD (4.95 mg/ml) was prepared as described in U.S. application Ser. No. 07/832,542, filed Feb. 5, 1992. The following formula was used:

| Ingredient | Amount (mg/ml) |
| --- | --- |
| BPD-MA | 4.95 |
| Dimyristoyl Phosphatidyl Choline | 23.27 |
| Egg Phosphatidyl Glycerol | 16.09 |
| Lactose or Trehalose | 148.50 |
| Ascorbyl Palmitate | 0.05 |
| Butylated Hydroxy Toluene | 0.005 |
| Water for Injection | Q.S. |

Liposomal BPD was dried and stored frozen at −20° C. in 1 ml aliquots. The appropriate number of aliquots were thawed immediately before use and diluted with 5% dextrose in water for injection into the animals.

Male Balb/c mice (7–11 weeks old; Charles River, Canada) were used in these studies, unless otherwise specified. Balb/c mice were chosen for the studies because of the lack of pigment in their skin. Shaving and depilation removed the hair very effectively from the entire body except the head. Then, the mouse skin appeared quite transparent. Internal organs, especially dark red organs such as liver and spleen, were visible through the skin. The mice were shaved and depilated with a commercially available depilator (Neet® or Nair®) 5 days before being used in the experiments. Control mice, injected with BPD but not exposed to light, were not shaved. Following injection the mice were kept in the dark for various lengths of time, as described below. Before and after the experiments the mice were kept in an animal facility with 12 hours of light and 12 hours of dark daily. After the experiments, in order to reduce the amount of light reaching the mice, their cages were placed on the lowest shelf with aluminum foil placed above them.

The light box was custom built at a workshop at the University of British Columbia. It was composed of two layers of 14 75 W tungsten-halogen reflector bulbs (General Electric), which illuminated the treatment area from the top and from the bottom. Light was filtered by 1) a set of filters comprising yellow and red plastic films which absorbed most of the light at wavelengths shorter than 600 nm and 2) 15 mm thick water filters which absorbed light above 900 rim. Cooling was provided by a steady flow of cold water in the water filters and by a set of 5 fans. The light intensity was measured by an IL 1350 Photometer (International Light).

Figure 1B:
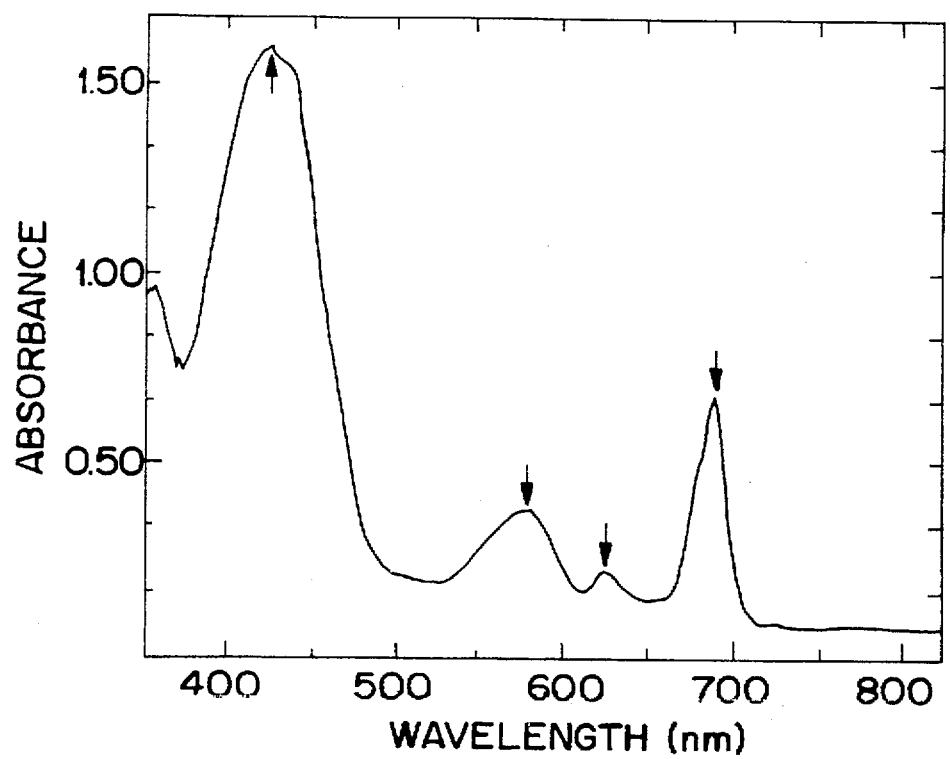
FIG. 1B shows the spectrum of light which activates BPD.

The light spectrum delivered by the light box is shown in FIG. 1A. For comparison the absorption spectrum of BPD is shown in FIG. 1B. Roughly ⅓ of the delivered light was within the BPD-activating spectral range.

The intensity of light delivered by the top and bottom sets of bulbs was not uniform. The bottom set delivered 33–40 mW/cm$^2$ as measured at floor level of the exposure chamber, while the top set delivered 27–33 mW/cm$^2$ as measured at the skin surface of the backs of the animals. The range described resulted from inconsistent influence at the horizontal plane of irradiation. In addition, mice moved about during light exposure, so that at various times different parts of their skin received different amounts of light. Therefore, the doses delivered to the surface of mice skin must be approximated and the calculations have been based on an intensity of 30 mW/cm$^2$.

Procedures

Blood Tests: Blood was drawn into syringes containing 50 µl of heparin (1000 units/ml saline). Blood samples (0.45 ml) from at least 1 mouse per time point were sent to the Diagnostic Laboratory at the University Hospital, University of British Columbia site, for analysis by a Coulter Counter. Blood morphology was determined on blood films prepared from selected samples by a laboratory technologist.

Determination of BPD Concentration in Plasma: Plasma samples were obtained by centrifugation of blood collected from mice and stored frozen at −20° C. until assessment. The concentration of BPD in the samples was determined by fluorometry using a Jasco Model FP-770 (Japan Spectroscopic Co.) spectrofluorometer and a microcuvette (Far UV Quartz Cell, Starna Cells Inc.). Excitation and emission wavelengths were 439 and 699 nm, respectively. Plasma samples were diluted 20-fold with PBS containing 1% Triton® X-100 immediately before fluorescence was determined. BPD standards were prepared in 5% mouse plasma in PBS with 1% Triton® X-100. Under these conditions the relationship between the concentration of BPD and units of fluorescence was linear (correlation coefficient>0.99) for concentrations between 0.1 ng/ml and 1 µg/ml. The limit of detection was below 0.1 ng/ml sample which corresponded to 2 ng/ml plasma. Maximum plasma autofluorescence was observed at 520 nm. The 699 nm fluorescence peak of BPD was virtually free from any interference.

EXAMPLE 1

Skin Photosensitivity Tests

Six Balb/c mice (22±1 g weight) were prepared as described above. Five mice were injected twice (24 hour interval) with BPD from DMSO stock (not liposomal BPD) and exposed to light 1 hour after the injection. One mouse was not injected but was exposed to light (light-only control). During the first treatment the mice were injected with 15 µg BPD/mouse in 200 µl of PBS. During the second treatment the mice were injected with 20 µg BPD/mouse (0.9 mg/kg). A single mouse was used as a control for both treatments.

Immediately post-injection (on both occasions) the animals were kept for 1 hour in the dark and then were placed in individual plastic containers (9×4×5 cm), which were placed in the light box and exposed to light. The individual mice were removed from the light box at different intervals: 15, 30, 45, 60 and 75 min, respectively. The light doses delivered at the surface of the skin were 27, 54, 81, 108 and 135 J/cm$^2$, respectively. On the second occasion the same light doses were used; however, mice receiving higher light doses on day 1 received lower doses on day 2. The control mouse was exposed to light for 60 min on both occasions. This is summarized in Table 1. During light exposure, the mice were constantly observed for signs of discomfort or itching. After the second light exposure, the mice were observed daily for a period of 2 weeks for appearance of the skin and general pattern of behavior.

Two weeks post-treatment blood samples were obtained from each mouse by a heart puncture, under halothane anesthesia. Then the mice were sacrificed and autopsied. Their spleen, liver and kidneys were weighed.

BPD-injected mice accepted all light doses delivered (27, 54, 81, 108 and 135 J/cm$^2$) and repeated treatment very well. On both days of treatment they behaved normally under the light, without any signs of discomfort, except for occasional scratching which could be caused by drug activation on the skin. No gross changes were observed in mice skin either immediately post-exposure or during the subsequent two week period. No behavioral changes were observed either. Surprisingly, the only mouse which showed signs of discomfort in the form of some agitation and scratching was the light-control mouse. Therefore, it was kept under the light for 60 min only (not 75 min, as originally planned).

The number of mice was too small to permit definitive conclusions to be drawn regarding the effect of the treatment on internal organs such as liver, spleen and kidneys; however in the test group, which was examined 2 weeks after the double treatment, gross morphology and weights were normal. The whole body weight and corresponding weight of organs are shown in Table 2.

Table 3 shows mouse blood parameters two weeks after treatment, including white blood cell count (WBC), red blood cell count (RBC), hemoglobin (HB), hematocrit (Hct), mean corpuscular volume (MCV), and platelet count (PLT). Blood cell morphology, determined 2 weeks post-treatment, is shown in Table 4. All values were within normal ranges. Platelet aggregation may have contributed to some slightly lower platelet counts and a higher WBC count.

TABLE 1

| Mouse No. | Day 1 (15 µg/mouse 0.68 mg/kg) | | Day 2 (20 µg/mouse 0.9 mg/kg) | |
| --- | --- | --- | --- | --- |
| | BPD mg/kg | Light J/cm$^2$ | BPD mg/kg | Light J/cm$^2$ |
| 1 | 0.75 | 27 | 1.0 | 135 |
| 2 | 0.71 | 54 | 0.95 | 108 |
| 3 | 0.71 | 81 | 0.95 | 81 |
| 4 | 0.63 | 108 | 0.87 | 54 |
| 5 | 0.71 | 135 | 0.95 | 27 |
| 6 | 0 | 108 | 0 | 108 |

TABLE 2

| Mice | Weight (g) | | | |
| --- | --- | --- | --- | --- |
| | Total Body | Liver | Spleen | Kidneys |
| Drug + Light | 22 | 1.105 | 0.077 | 0.172 (1) |
| | 23 | 1.190 | 0.106 | 0.343 |
| | 24 | 1.208 | 0.094 | 0.380 |
| | 25 | 1.348 | 0.108 | 0.396 |
| | 21 | 0.958 | 0.078 | 0.310 |
| Light Only | 22 | 1.125 | 0.05 | 0.371 |

TABLE 3

| Mouse No. | WBC 10$^6$/ml | RBC 10$^9$/ml | HB g/l | Hct | MCV fl | PLT 10$^6$/ml |
| --- | --- | --- | --- | --- | --- | --- |
| 1 | 4.0 | 7.11 | 122 | 0.352 | 49.5 | 328 |
| 2 | 14.7* | 7.76 | 126 | 0.382 | 49.2 | 274 |
| 3 | 8.2 | 7.46 | 124 | 0.365 | 48.9 | 119 |
| 4 | 7.6 | 7.65 | 123 | 0.364 | 47.6 | 438 |
| 5** | 2.9 | 6.47 | 108 | 0.316 | 48.8 | 134 |
| 6*** | 5.3 | 5.97 | 109 | 0.297 | 49.8 | 388 |

*platelet aggregate may contribute to this number
**some evidence of blood having been diluted with a double volume of heparin
***control light only

TABLE 4

| Mouse No. | % WBC | | |
| --- | --- | --- | --- |
| | Granulocytes | Lymphocytes | Monocytes |
| 1 | 9 | 90 | 1 |
| 2 | 11 | 88 | 1 |
| 3 | 19 | 78 | 3 |
| 4 | 36 | 62 | 2 |
| 5 | 7 | 92 | 1 |
| Normal (Range) | 12–15 | 65–85 | N/A |

EXAMPLE 2

Pharmacokinetic (PK) Studies

Figure 2:
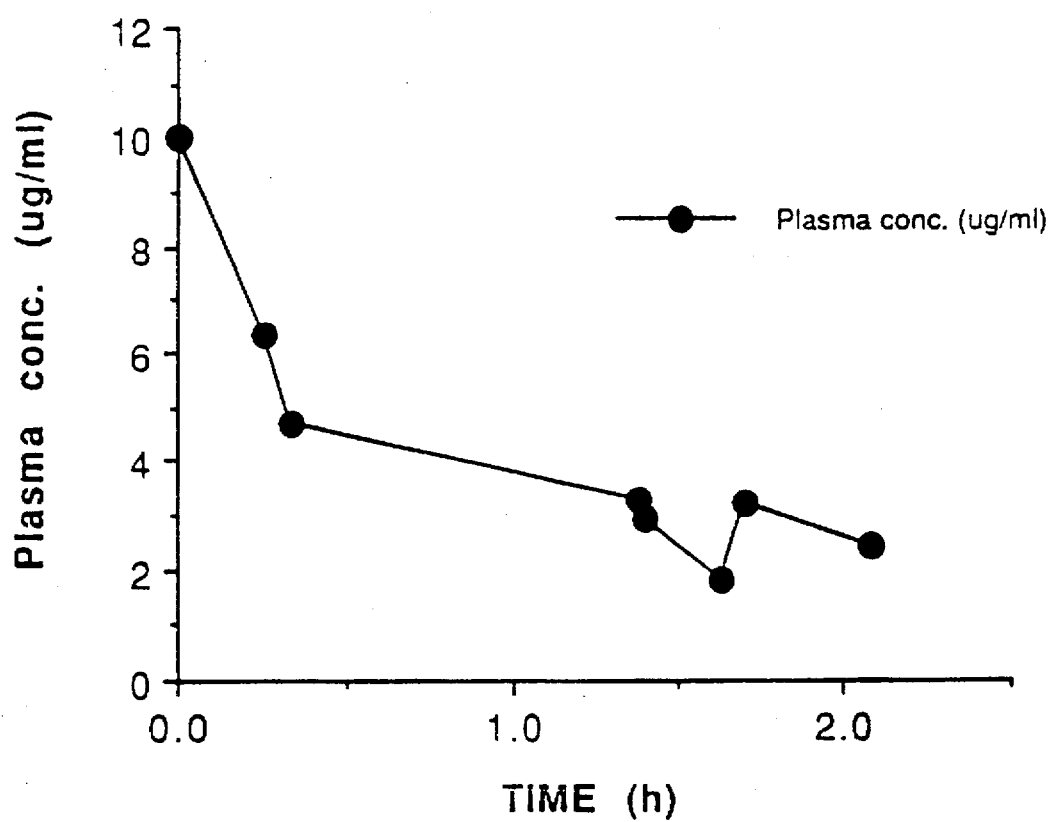
FIG. 2 displays the concentration of BPD in mouse plasma at various times following injection of liposomal BPD at 20 µg/mouse (0.9 mg/kg).

In order to determine the level of BPD in plasma during the light treatment, the following experiment was carried out. Fourteen Balb/c mice (22±1 g of weight) were injected with liposomal BPD at 20 µg/mouse (0.9 mg/kg) in 200 µl PBS per mouse. Blood samples were obtained by heart puncture at various time intervals between 15 min and 2 hours post-injection. Exposure to light started at 15 min post-injection for some mice. The BPD concentration in plasma was determined as described above. The results are presented in Table 5 and FIG. 2.

These data were used to test the effect of timing of light exposure. At 2 hours post-injection, i.e., at the time point corresponding to the end of 1 hour exposure to light (108 J/cm$^2$) in the first example, the plasma level of BPD was 2.44 µg/ml. At the beginning of exposure to light, in the same example, the plasma level of BPD was about 4 µg/ml. To further evaluate skin photosensitivity at these low levels, mice were exposed to light at an earlier time post-injection, i.e., at 15 min, when the level of BPD in plasma was 6.32 µg/ml. However, mice beginning light exposure at 15 minutes were almost immediately uncomfortable and died after 30 min of exposure (54 J/cm$^2$). This indicated that a starting plasma level of BPD of about 6.5 µg/ml and light exposure of about 50 J/cm$^2$ whole body irradiation were lethal to mice. However, as demonstrated in Example 1, when plasma levels are lower, the same light dose is apparently harmless.

TABLE 5

| Mouse No. | Dose BPD mg/kg | Time Post Injection | Plasma Conc. (µg/ml) |
|---|---|---|---|
| 1 | 0.87 | 15 min | 6.32 |
| 2 | 0.83 | 20 min | 4.68 |
| 3 | 0.95 | 1 h 23 min | 3.26 |
| 4 | 0.91 | 1 h 24 min | 2.92 |
| 5 | 0.91 | 1 h 32 min | 2.98 |
| 6 | 0.87 | 1 h 38 min | 1.80 |
| 7 | 0.87 | 1 h 42 min | 3.22 |
| 8 | 0.83 | 2 h 5 min | 2.44 |

EXAMPLE 3

Transcutaneous Activation of BPD

Fourteen mice (weight 22±1 g) were used in this study. Twelve mice were injected with 20 µg (0.9 mg/kg) of liposomal BPD (in 200 µl) and kept in the dark for 1 hour before exposure to light. The mice each were exposed to light for 30 min, 1 hour or 1.5 hours, which delivered light doses to the skin surface of 54, 108 and 162 J/cm$^2$, respectively. Immediately after light exposure, blood samples were obtained. At the corresponding times, blood samples were obtained from two mice injected with BPD, but not exposed to light. Two additional mice were tested one hour after injection.

The aim of this study was to determine light penetration of the tissues to activate BPD. It was assumed that the substantial photodegradation of BPD in blood would represent substantial activation of BPD.

Figure 3:
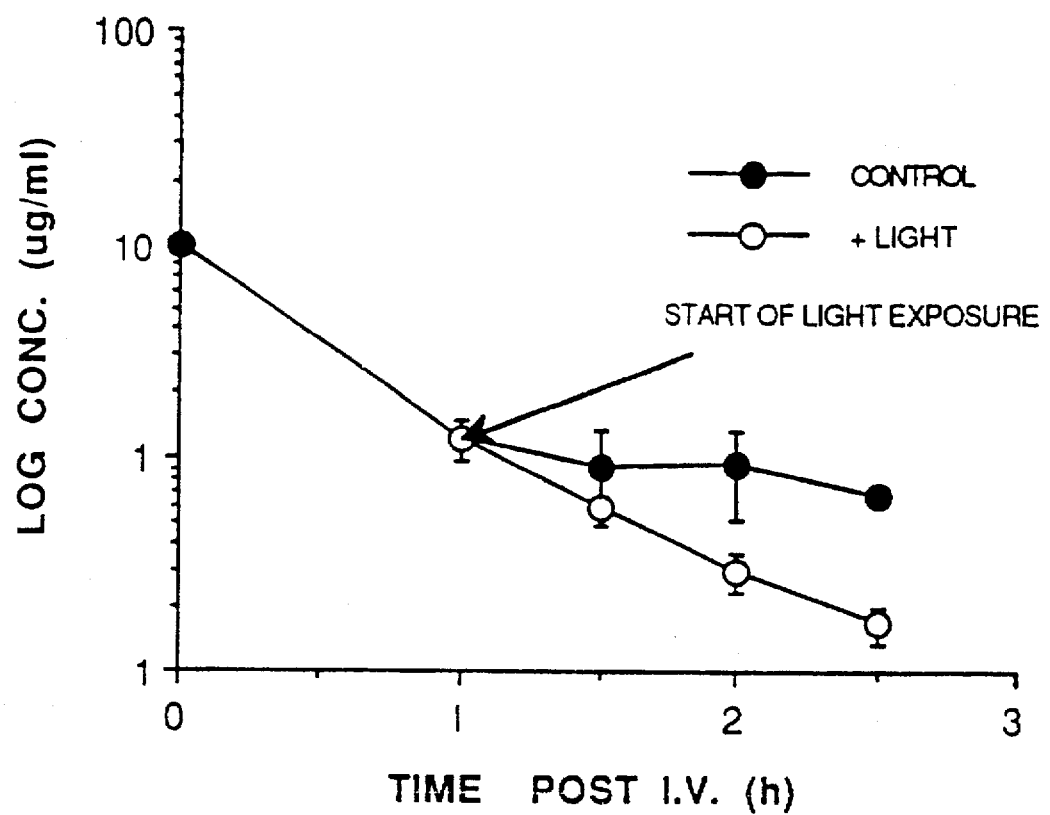
FIG. 3 displays the concentrations of BPD in mouse plasma at various times following injection of liposomal BPD at 20 µg/mouse (0.9 mg/kg) for mice exposed to light and control mice kept in the dark.

The BPD plasma concentration was then determined by fluorescence. The concentrations of unchanged BPD in the plasma of exposed and unexposed control mice were compared. The results (presented in Table 6 and FIG. 3) showed that 36–76% of BPD was photodegraded by light doses of 54–162 J/cm$^2$. This amount of photodegradation indicated that sufficient light penetrated the tissues and activated and thereby degraded BPD in blood vessels. Importantly, these light exposures and drug doses did not cause skin photosensitivity, which confirmed the safety found in Example 1. Moreover, no acute effect on blood parameters was observed (Table 7).

TABLE 6

| Group | Light Dose J/cm$^2$ | Time Post Injection | BPD in Plasma µg/ml | Mean ± SD | Photodegraded BPD (%) |
|---|---|---|---|---|---|
| 0 h - C | 0 | 1 h | 1.428 1.058 | 1.243 ± 0.262 | — |
| 30 min - C | 0 | 1½ h | 0.618 1.242 | 0.930 ± 0.441 | — |
| 1 h - C | 0 | 2 h | 0.646 1.242 | 0.944 ± 0.421 | — |
| 1½ h - C | 0 | 2½ h | 0.724 0.656 | 0.690 ± 0.048 | — |
| 30 min | 54 | 1½ g | 0.566 0.626 | 0.596 ± 0.042 | 36% |
| 1 h | 108 | 2 h | 0.258 0.344 | 0.301 ± 0.061 | 68% |
| 1½ h | 162 | 2½ h | 0.191 0.145 | 0.168 ± 0.033 | 76% |

| BPD mg/kg | Light J/cm$^2$ | Time Post Inj. | WBC 10$^6$/ml | RBC 10$^9$/ml | HB g/l | Hct | MCV fl | PLT 10$^6$/ml |
|---|---|---|---|---|---|---|---|---|
| 0 | 0 | — | 4.5 | 6.58 | 113 | 0.326 | 49.5 | 417 |
| 0 | 0 | — | 2.3 | 7.53 | 127 | 0.370 | 49.1 | 399 |
| 0 | 0 | — | 6.0 | 7.61 | 132 | 0.378 | 49.7 | 498 |
| 0 | 0 | — | 7.3 | 7.64 | 133 | 0.382 | 50.0 | 613 |
| 0.87 | 0 | 1 h | 5.5 | 7.61 | 124 | 0.368 | 48.4 | 608 |
| 0.87 | 0 | 1½ h | 4.4 | 6.77 | 117 | 0.329 | 48.7 | 428 |
| 0.93 | 0 | 2 h | 11.4 | 7.79 | 129 | 0.382 | 49.1 | 475 |
| 0.87 | 0 | 2½ h | 3.9 | 7.68 | 129 | 0.372 | 48.5 | 447 |
| 0.95 | 54 | 1½ h | 7.0 | 7.28 | 127 | 0.363 | 49.9 | 613 |
| 0.95 | 108 | 2h | 8.5 | 7.53 | 131 | 0.378 | 50.1 | 440 |
| 0.93 | 162 | 2½ h | 4.9 | 7.17 | 116 | 0.353 | 49.2 | 506 |

The data obtained in this example were compared with those in previously published studies (*Photochem. Photobiol.* (1991) 53:281–286), after the light dosimetry was recalculated using the same photometer as used in the present study. In the previously published studies, DBA/2 mice (shaved and depilated) were injected at 4 mg/kg and were exposed locally to 153 J/cm$^2$ broad spectrum light (intensity 170 mW/cm$^2$) at 3 hours post-injection. Extrapolating from FIG. 2 would yield a maximum plasma concentration at three hours (the beginning of a 30 min light exposure) of 2.987±0.312 (SD) µg/ml. As a result, although no immediate post-exposure changes in the skin were observed, within the first 24 hour post-exposure, mice developed severe skin necrosis which progressed for up to 96 hours and was followed by a healing period. Eventually the wounds healed and the hair regrew.

In the present study plasma concentrations of BPD at the beginning of exposure to light were above 3 µg/ml and yet no changes of the skin were observed either immediately or during the 2 week post-exposure period. The differences between the previous and the present studies include (1) higher maximum plasma concentration due to the higher dose of BPD (4 mg/kg versus 0.9 mg/kg), (2) longer time between the injection and exposure to light (3 hours versus 1 hour), which allowed more accumulation of BPD in the skin (BPD apparently accumulated in the skin for up to 5 hours), and (3) higher intensity of light (170 mW/cm$^2$ versus 30 mW/cm$^2$). The data suggest that all these factors must be considered in defining a therapeutic window for whole body irradiation.

EXAMPLE 4

In Vitro Activation of BPD in Mouse Blood

In order to assess the amount of light penetrating the tissues, in vitro experiments with mouse blood were carried out. The same light source was used, therefore the spectrum of light was the same. The light doses in this experiment were selected to mimic the doses in the in vivo experiments.

Liposomal BPD was added to freshly obtained heparinized mouse blood to achieve a concentration of 1 µg/ml, following which 0.85 µl aliquots of blood were dispensed into 35 mm diameter petri dishes, which were placed in the light box and exposed to red light. The dishes were irradiated in the light box from below only. The intensity of light was 35 mW/cm$^2$. Three different light doses, entailing exposure of 30 min, 1 hour and 1.5 hour, were 63, 126 and 189 J/cm$^2$, respectively. Duplicate dishes were kept covered with aluminum foil. Immediately following light exposure, the blood was collected from the dishes. Then the plasma was separated by centrifugation. The control unexposed samples were processed at time points corresponding to the light exposed samples.

Figure 4:
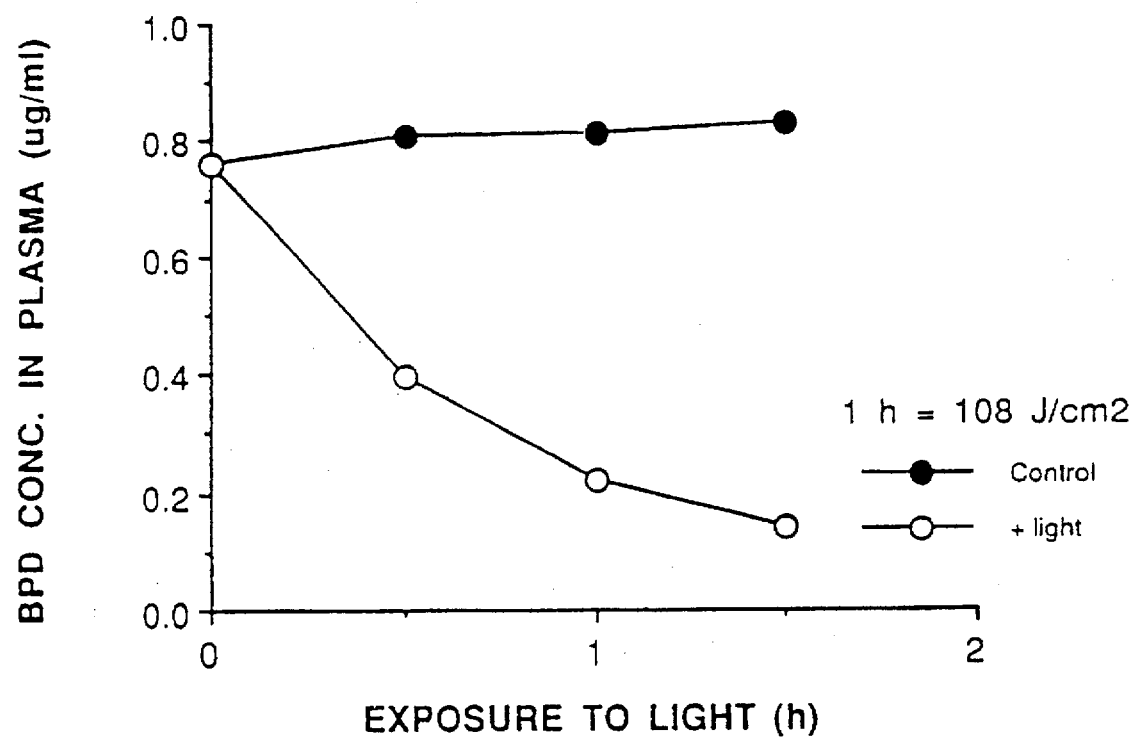
FIG. 4 shows in vitro photodegradation of BPD (1 µg/ml) in mouse blood exposed to light for various times.

The concentration of BPD in plasma separated from light-exposed and unexposed blood was determined by fluorescence. The results are presented in Table 8 and FIG. 4. About 51–83% of BPD was degraded by the ranges of light doses used.

Figure 5:
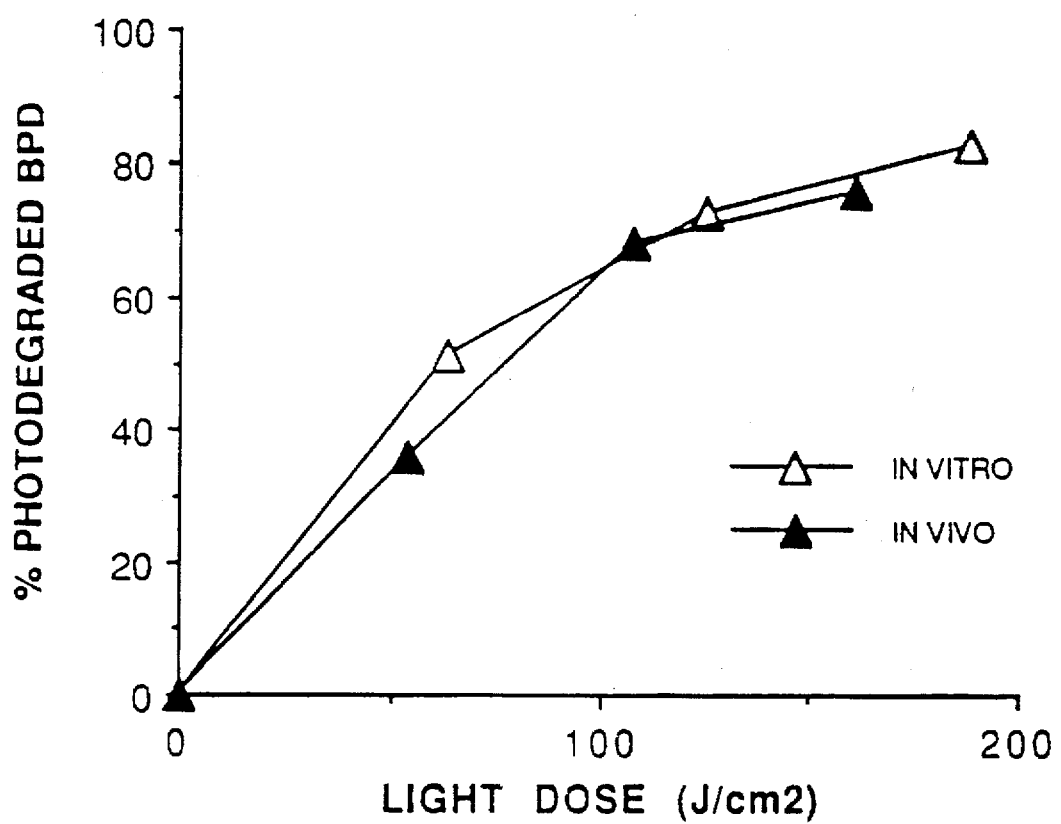
FIG. 5 graphs the percentage of BPD photodegraded in mouse blood in vivo and in vitro by exposure to light in comparison to unexposed blood.
Figure 6:
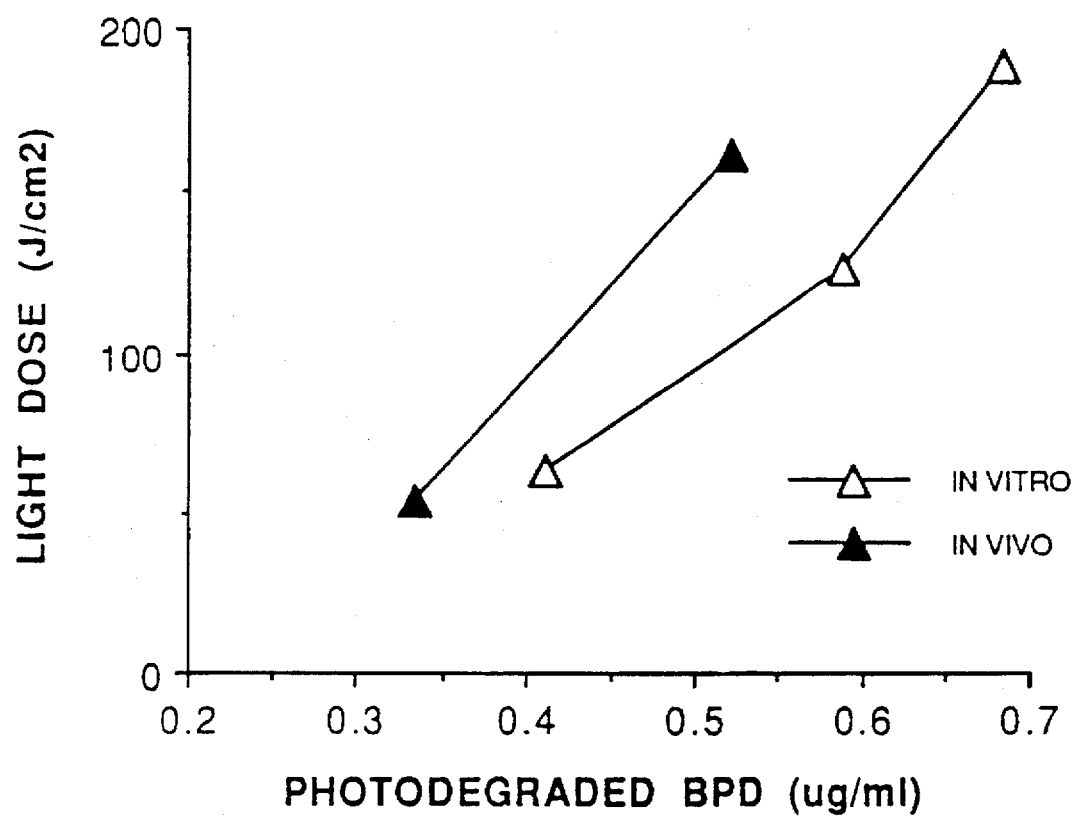
FIG. 6 graphs the amount (µg/ml) of BPD photodegraded in mouse blood exposed to red light (600–900 nm) in vitro and in vivo (whole body irradiation) in comparison to unexposed blood.

The extent of photodegradation of BPD in vitro was compared with in vivo degradation to estimate the amount of light actually penetrating the tissues and reaching BPD in blood vessels. When the amounts of photodegraded BPD in both experiments were expressed as percentage degradation in relation to the amount of unchanged BPD present in plasma in the absence of light, the percentages determined in vitro and in vivo were relatively similar (Table 9, FIG. 5). However, when the amounts of degraded BPD were compared as µg photodegraded BPD per ml of plasma it became obvious that about 65% of the light dose delivered to the surface of skin in vivo actually reached BPD in the blood vessels (Table 9, FIG. 6).

TABLE 8

| Time | Light Dose J/cm$^2$ | BPD Dose µg/ml | Photodegraded BPD % |
|---|---|---|---|
| 0 h | 0 | 0.760 | — |
| ½ h | 0 | 0.806 | — |
| ½ h | 63 | 0.394 | 51% |
| 1 h | 0 | 0.810 | — |
| 1 h | 126 | 0.220 | 73% |
| 1½ h | 0 | 0.830 | — |
| 1½ h | 189 | 0.144 | 83% |

TABLE 9

| IN VITRO | | | IN VIVO | | |
|---|---|---|---|---|---|
| Light (J/cm$^2$) | Photodegraded % | Dose µg/ml | Light (J/cm$^2$) | Photodegraded % | Dose µg/ml |
| 63 | 51 | 0.412 | 54 | 36 | 0.334 |
| 126 | 73 | 0.590 | 108 | 68 | 0.643 (?) |
| 189 | 83 | 0.686 | 162 | 76 | 0.522 |

In order to determine the level of BPD in plasma during the light treatment the following experiment was carried out.

The results of the preceding examples indicate that there is a therapeutic window for activation of BPD in blood by means of whole body irradiation. After mice were exposed to red light (600–900 nm) for 1 hour after injection of BPD at 0.9 mg/kg, at the range of light doses between 27 to 135 J/cm$^2$ (light intensity at skin level was about 30 mW/cm$^2$), the mice did not show any signs of skin photosensitization for two weeks after treatment. Moreover, no toxicity was detected during gross examination of the liver, spleen, and kidneys, or from changes in blood parameters as determined 2 weeks post-treatment. The approximate plasma levels during the exposure to light were between 2.5 and 4 µg/ml.

The highest plasma concentration of BPD (6.3 µg/ml immediately after administration) in combination with 54 J/cm$^2$ light was lethal to mice. The exposure to light in vivo resulted in 36–76% photodegradation of BPD in blood. Comparison with the in vitro photodegradation of BPD in mouse blood indicated that approximately 65% of the dose delivered to the surface of skin penetrated mouse tissue to reach BPD inside blood vessels. Comparison of these data with the previously published studies indicated that skin photosensitivity is determined by the maximum plasma concentration, the time of exposure to light in relation to injection, and the intensity of light.

EXAMPLE 5

Male mature DBA/2 and Balb/c mice were injected intravenously with P815 and L1210 cells, respectively, preincubated for 1 hour with BPD (liposomal) at 100 ng/ml. Immediately before animal injection, an additional 2 µg of BPD was added to the syringes containing cells. This resulted in the concentration of 1 µg BPD/ml mouse plasma immediately post-injection (assuming the total volume of mouse blood is about 2 ml). One group of mice (shaved and depilated) was exposed immediately to red light (600–900 nm) in the light box for 1.5 hours (162 J/cm$^2$); the other group was kept in the dark as the control.

Immediately after exposure to light, blood samples were obtained by a heart puncture under halothane anesthesia. The concentration of BPD in plasma of light-exposed and control mice was determined by fluorescence. The number of clonogenic tumor cells in mouse blood was determined by culturing blood samples in culture medium supplemented with 10% bovine serum, using a limiting dilution assay protocol. After treatment, a number of mice from both control and experimental groups were observed for skin changes and general behavior for up to two weeks. The results are summarized in Tables 10 and 11.

TABLE 10

Balb/c Mice Injected with L1210 Cells 1 Hour with BPD Liposomes

| | BPD Concentration in Plasma | |
|---|---|---|
| Treatment | ng/ml | % |
| Dark control | 126.45 | 100% |
| Light exposed | 52.23 | 41% |
| Percent photodegraded: | | 59% |

Surviving cells in blood (average of 3 mice/group):
Dark control: 234 L1210 cells/2 ml blood/mouse
Light exposed: 21 L1210 cells/2 ml blood/mouse

TABLE 11

DBA/2 Mice Injected with P815 Cells

| Treatment | BPD in Plasma | |
|---|---|---|
| | ng/ml | % |
| Dark control | 94.09 | 100% |
| Light exposed | 58.14 | 62% |
| Percent photodegraded: | | 38% |

Surviving cells in blood (average of 3 mice/group)
Dark control: 50 P815 cells/2 ml blood/mouse
Light exposed: 8 P815 cells/2 ml blood/mouse The results in the preceding examples showed that whole body exposure to red light, following injection of BPD, caused activation of BPD in the blood. As a result, some of BPD was photodegraded and, at the same time, a large number of BPD pre-loaded tumor cells were destroyed. After treatment neither skin photosensitivity nor change in the behavior of animals were observed (maximum observation period was 2 weeks). The results indicate the existence of a therapeutic window whereby the therapeutic control of blood-borne infectious agents could be affected, without damaging the blood vessels and skin.

This invention has been described by a direct description and by examples. As noted above, the examples are meant to be only examples and not to limit the invention in any meaningful way. Additionally, one having ordinary skill in this art in reviewing the specification and claims which follow would appreciate that there are equivalents to those claimed aspects of the invention. The inventors intend to encompass those equivalents within the reasonable scope of the claimed invention.

I claim:

1. A method to destroy or impair target cells in the bloodstream of a subject, which method comprises:

(a) administering to said subject a photosensitizing agent in an amount sufficient to produce a concentration of photosensitizing agent or, if the photosensitizing agent is a prodrug, a concentration of the photosensitizing agent product of the prodrug, within the subject's bloodstream, of about 0.01 to 100 µg/ml;

(b) allowing to elapse a post-injection time sufficient to allow homing of the photosensitizing agent to the target cells while still maintaining said photosensitizing agent concentration in the bloodstream; and (c) irradiating at least a portion of said subject with light of a wavelength absorbed by said photosensitizing agent or, if the photosensitizing agent is a prodrug, by the product thereof, wherein said irradiating is conducted transcutaneously;

and wherein the concentration of photosensitizing agent in the bloodstream of the animal, the post-injection time, the intensity of the light, and the duration of said irradiating step, are all such that the target cells in the bloodstream are selectively impaired or destroyed while skin photosensitivity is substantially avoided.

2. The method of claim 1 wherein said photosensitizing agent is selected from the group consisting of a chlorin, a bacteriochlorin, a phthalocyanine, a porphyrin, a benzoporphyrin, a purpurin, a merocyanine, a psoralen, and the prodrug amino levulunic acid (ALA).

3. The method of claim 1 wherein said photosensitizing agent is a porphyrin, a benzoporphyrin or ALA.

4. The method of claim 2 wherein the porphyrin is porfimer sodium and the benzoporphyrin is BPD.

5. The method of claim 1 wherein said target cells are leukemic cells, virus-containing cells, parasite-containing cells, or microorganisms.

6. The method of claim 1 wherein said concentration within the animal's bloodstream is about 0.01 to 10 µg/ml.

7. The method of claim 1 wherein said concentration within the animal's bloodstream is about 0.01 to 4 µg/ml.

8. The method of claim 1 wherein said concentration within the animal's bloodstream is about 0.01 to 2 µg/ml.

* * * * *